United States Patent [19]

Zimble

[11] Patent Number: 4,950,163
[45] Date of Patent: Aug. 21, 1990

[54] DENTAL SYRINGE FOR TREATING GUMS

[76] Inventor: Alan W. Zimble, 2006 Limestone Rd. #2, Wilmington, Del. 19808-5553

[21] Appl. No.: 195,791

[22] Filed: May 19, 1988

[51] Int. Cl.$^5$ ................................................ A61C 5/00
[52] U.S. Cl. .................................... 433/215; 433/89
[58] Field of Search .................. 433/90, 89, 80, 81; 604/131, 134, 135, 136, 229, 209, 210

[56] References Cited

U.S. PATENT DOCUMENTS

| | | | |
|---|---|---|---|
| 1,340,043 | 5/1920 | Grace . | |
| 2,188,449 | 1/1940 | Stewart . | |
| 2,369,304 | 2/1945 | Lewis | 604/209 |
| 2,875,761 | 3/1959 | Helmer et al. | 604/210 |
| 3,807,048 | 4/1974 | Malmin | 32/40 |
| 3,816,421 | 6/1974 | Malmin | 433/81 |
| 3,949,748 | 4/1976 | Malmin | 433/81 X |
| 3,995,629 | 12/1976 | Patel | 604/227 X |
| 4,276,880 | 7/1981 | Malmin | 604/264 X |
| 4,381,006 | 4/1983 | Genese | 604/135 |
| 4,512,769 | 4/1985 | Kozam et al. | 433/80 X |
| 4,592,746 | 6/1986 | Burkholder et al. | 604/220 |
| 4,636,197 | 1/1987 | Chu | 604/131 |
| 4,642,102 | 2/1987 | Ohmori | 604/210 |

FOREIGN PATENT DOCUMENTS

| | | | |
|---|---|---|---|
| 711528 | 6/1965 | Canada | 604/210 |
| 0208975 | 1/1987 | European Pat. Off. | 604/210 |

Primary Examiner—Robert P. Swiatek
Assistant Examiner—Nicholas D. Lucchesi
Attorney, Agent, or Firm—Connolly & Hutz

[57] ABSTRACT

A syringe for treating gums includes a cylinder in which a piston is reciprocally mounted. The fluid for treating the gums is located in the cylinder and is expelled from a spout, such as a cannula or other replaceable reusable thin irrigating tip. The tip would have a rounded end if made of metal and would be softer if made of plastic thus rendering it relatively harmless, while thin enough to provide access to the deepest regions of the periodontal pocket and deposit/irrigate effective antibacterial agents so as to eradicate periodontal disease associated micro-organisms. Fluid is discharged by depressing the piston into the cylinder. A resilient member reacts means react between the piston and the cylinder to urge the piston into the cylinder. The user may control the amount of inward movement by manually restraining the piston.

1 Claim, 2 Drawing Sheets

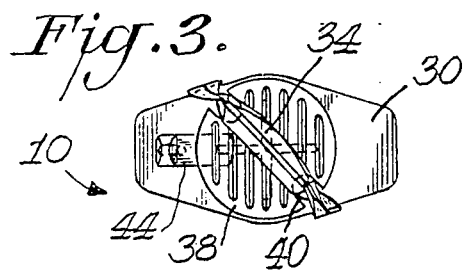
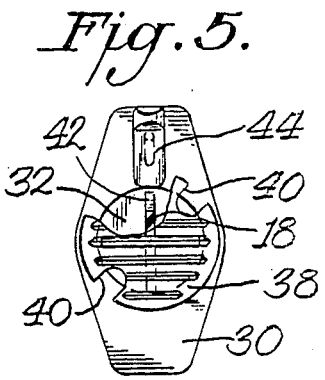
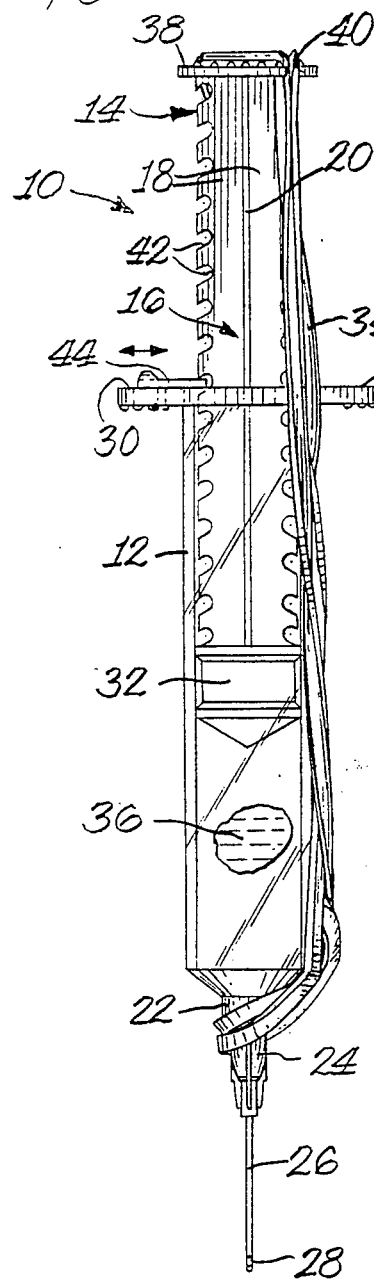
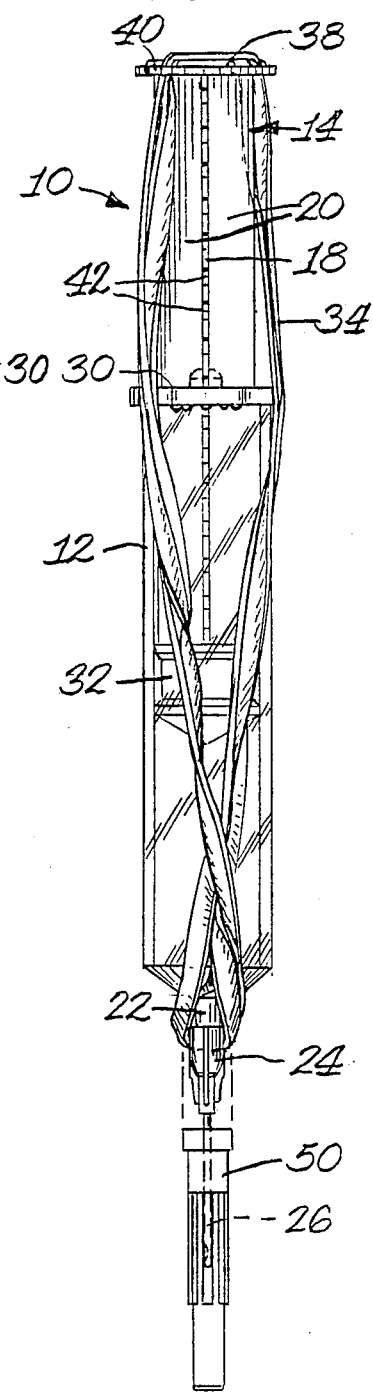
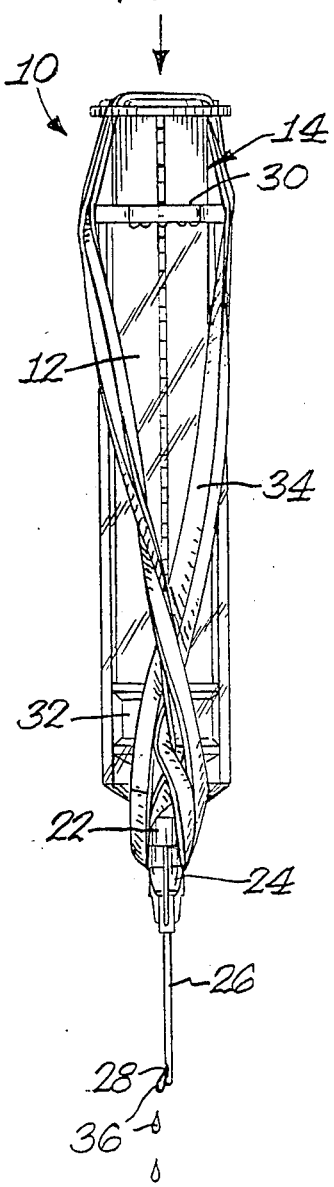

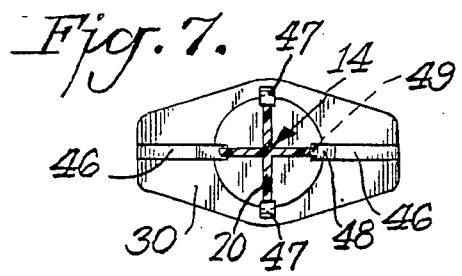
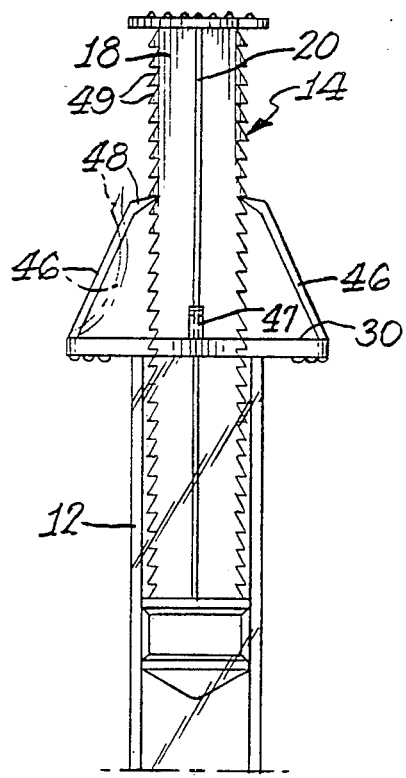

DENTAL SYRINGE FOR TREATING GUMS

BACKGROUND OF INVENTION

The present invention is concerned with a syringe for treating gums, particularly a syringe which could be for home or away from the office use. A known liquid treating device for home use is the conventional Water-Pik. Such device needs an electrical source to provide a constant rapidly pulsating flow of fluid from a reservoir through an applicator which is placed in the mouth. Another device for treating the gums is the IMAX applicator from Stram Dental and other's similar devices. The IMAX applicator is in the form of a squeeze bottle having a spout screwed thereon with the applicator itself being a hollow cannula. While these devices have some utility, it would be desirable if a device could be provided sufficiently low in cost as to be disposable, yet sturdy enough in manufacture that it could be repeatedly used and not require the instability inherent in having to place and squeeze a device or have to control relatively heavy pulsating streams of fluid which tend to flood the areas and make it difficult to control placement and use.

Other devices of interest are described in U.S. Pat. Nos. 1,340,043; 1,610,831; 2,188,449 and 3,807,048.

SUMMARY OF INVENTION

An object of this invention is to provide a dental syringe for treating gums which is particularly adaptable for home or away from office use because it is very portable and can be taken wherever the user goes.

A further object of this invention is to provide such a dental syringe wherein the flow of fluid against the gums is achieved automatically, but the flow could be interrupted or controlled by manual operation from the user.

In accordance with this invention a syringe is provided in the form of a cylinder in which a piston is mounted. A piston is a plunger having a piston head at one end which moves reciprocally in the cylinder to cause the fluid therein to be discharged from a spout which is in the form of a cannula or thin plastic tip. The plunger has an endplate at its end opposite the piston head. In accordance with the invention, resilient means, such as a rubberband of selected size and elasticity is secured to the endplate and secured to the cylinder so as to create a resilient force which urges the piston head downwardly into the cylinder and thus automatically causes the fluid to be discharged into the gum or gingival crevice pocket. The cylinder has a pair of flanges against which finger pressure may be applied to resist the inward motion of the piston. If it is desired to halt the flow of fluid or slow down the flow, the user may simply manually resist the resilient force squeezing the piston while applying finger pressure to the flanges to apply a frictional force to oppose the resilient force from the resilient means.

In one form of this invention, the endplate has a pair of notches for receiving the resilient means, and the hub of the cylinder where the spout or cannula extends therefrom may be utilized as the location for anchoring the opposite end of the resilient means.

The fluid for treating the gums may be a fluid containing anti-microbial agents into the gingival pocket or gingival sulcus as a device to prevent and eradicate periodontal disease at the active disease site.

THE DRAWINGS

FIG. 1 is a front elevation view of a dental syringe in accordance with this invention;

FIG. 2 is a side elevation view of the syringe shown in FIG. 1 and further indicating a safety closure;

FIG. 3 is a top plan view of the syringe shown in FIGS. 1-2;

FIG. 4 is a side elevation view similar to FIG. 2 in a different stage of operation;

FIG. 5 is a top plan view of the syringe of FIGS. 1-4 with the end plate partially broken away and with the resilient means removed;

FIG. 6 is a side elevation view of a modified syringe in accordance with this invention; and FIG. 7 is a top plan view partly in section of the syringe shown in FIG. 6.

DETAILED DESCRIPTION

As shown in FIGS. 1-5 in one embodiment of this invention a dental syringe 10 includes a cylinder 12 into which a piston 14 is reciprocally mounted. Piston 14 includes a plunger 16 in the form of four struts 18, 18 and 20, 20. The pair of struts 18, 18 are arranged in line with each other and perpendicular to the intermediate struts 20, 20.

Syringe 10 also includes a hub portion 22, extending from cylinder 12 at the dispensing end. Hub portion 22 in turn includes a needle holder 24 or fitting end of the delivery tip and applicating cannula or thin plastic dispensing tip 26 which is hollow and which has a dispensing opening 28 at or near its remote end. The applicating device is preferably a cannula or other replaceable reusable thin irrigating tip. The tip would have a rounded end if made of metal and would be softer if made of plastic thus rendering it relatively harmless, while thin enough to provide access to the deepest regions of the periodontal pocket and deposit/irrigate effective anti-bacterial agents so as to eradicate periodontal disease associated micro-organisms. A pair of flanges 30, 30 extend outwardly from the remote end of cylinder 12.

The general arrangement of the cylinder 12 with a piston 14 and a piston head 32 as well as the dispensing cannula is known in the art. Such syringes are readily available commercially in various sizes but without the resilient means (later described) to dispense the fluids. Similarly, the leur-lok type hubs and cannulas are also readily available. The present invention modifies that arrangement in a number of respects. Specifically, in accordance with the invention, as later described, resilient means (which is the basis of the invention) are provided so that a force is established for causing the automatic dispensing of the fluid from cylinder 12 through dispensing opening 28 not requiring any action other than accurate placement by the user except when the user desires to stop it. Additionally, the use of the syringe in the manner of this invention differs from the conventional use of such syringe, which in turn results in certain structural modifications.

With the use of a syringe having a capacity of 20 cc, a patient should be able to irrigate many sites before needing refilling.

As shown in FIGS. 1-5 a resilient means 34 in the form of an endless elastic member of rubberband is provided to cause the piston 14 to move inwardly in cylinder 12 so that piston head 32 forces the fluid 36 to be dispensed from opening 28 (as shown in FIG. 4).

The piston 14 includes at its end remote from piston head 32 and end plate 38 which is of circular dimension, but which includes a prepared pair of notches 40, 40 (see FIG. 5). The notches 40 provide locations for receiving the rubberband 34, with the free ends of the rubberband being positioned over the hub 22 at the opposite end of cylinder 12. In this manner, the rubberband is stretched when piston 14 is in its outwardmost position and the tendency of the rubberband to contract provides the resilient force for urging the fluid 36 out of cylinder 12.

In accordance with this invention a braking action which may either completely stop or which may slow the inward movement of piston 14 may be manually provided by the user simply squeezing plunger 16 while the user's fingers press against the flanges 30, 30 to resist the force of resilient means or rubberband 34.

In accordance with this invention means are provided to slow or stop plunger 14 at various locations. The means of FIGS. 1-5 involves providing a series of inclined notches or teeth 42 in the edges of the pair of struts 18, 18. The notches 42 may be used for selectively receiving a movable stop member. FIGS. 1 and 5, for example, shows the stop member to be an arm 44 which is rotatably mounted to one of the flanges 30 for rotational movement into a selective notch 42.

FIGS. 6-7 show an alternative embodiment of this invention wherein a pair of spring arms 46 are mounted to cylinder 12 having the ends 48 operating in the manner of a pawl which engages the ratchet teeth or of notches 49.

Since struts 18, 18 have teeth, squeezing these struts would be uncomfortable. Accordingly, intermediate struts 20, 20 are smooth to provide more convenient gripping surfaces. If desired smooth gripping surfaces may be created by filling in regions between the struts. Such filled-in portions may have a roughened surface so that the fingers will not tend to slip when contacting such portions.

FIGS. 6-7 illustrate a further feature which may also be incorporated in the prior embodiment. That feature is the provision of short rails or tracks 47 in which struts 20, 20 are disposed to prevent piston 14 from rotating. This assures proper alignment of the locking mechanism with the teeth in struts 18, 18. Such rotation — preventing rails 47 function as a safeguard since the placement of the rubberband itself on the syringe would prevent rotation of the piston 14.

The rate of flow or resistance to the piston action can also be controlled by the size of the lumen of the cannula or other access tip. Syringe 10 is also advantageous in that it can apply the treating fluid without having to fight gravity on the upper jaw as required by conventional squeezing devices.

FIG. 2 also illustrates the provision of a tubular protector 50 which snaps over cannula 24 for shielding the cannula during periods of non-use. Protector 50 is of the type conventionally used with hypodermic syringes.

In use cylinder 12 would be filled with an appropriate fluid by the conventional aspiration techniques or by disassembling syringe 10 to remove the plunger 14 from cylinder 12. The fluid 36 may simply be water or may be any suitable fluid containing, for example, anti-microbal agents which would be directed into the gingival pocket or gingival sulcus as an aid to preventing periodontal disease and also treat active periodontal disease. The rubberband 34 would be mounted on device 10 by positioning central portions of the rubberband in notches 40, 40 and then looping the free ends of the rubberband around hub 22. It is to be understood that any suitable form of resilient means may be used and that the invention is not limited to a rubberband as the resilient means. The use of a rubberband, however, is particularly desirable since such rubberbands are readily available in various lengths and in various resilient strengths. When the rubberband is mounted on device 10, it then provides a resilient force which urges plunger 14 into cylinder 12. When it is desired to completely stop or to slow the application of the fluid against the gums the user applies finger pressure to flanges 30 while squeezing plunger 14. In this manner, the user can control the amount of the fluid being dispensed from device 10. The flow additionally can be completely stopped by locking plunger 14 at any of a number of locations through the use of a suitable locking mechanism such as illustrated in FIGS. 1 and 6. Device 10 applies the fluid to the suitable hollow needle 26 having a rounded point with a dispensing opening 28.

Dental syringe 10 provides a manner of accurately delivering the desired amount of treating fluid to specific sites in the user's mouth and lends itself to economical mass production including the use of known parts such as the syringe with its cylinder and plunger which need be modified only slightly for accommodating the rubberband and the locking mechanism. Additionally, the use of rubberbands is desirable because of their ready availability to provide the desired resilient force.

Device 10 may be made of sufficiently low cost as to be of single use and disposable. Alternatively, device 10 is made sufficiently sturdy and may be readily assembled and disassembled for multiple use. Device 10 is particularly advantageous in that its applicating tip can get close to the base of the disease pocket to eradicate bacteria or can get in the non-diseased pocket to prevent further periodontal destruction. Thus, application of treating fluid would be at the apical-most portion where destruction of the tooth support is actively taking place.

What is claimed is:

1. A method of treating a user's gums comprising the steps of supplying a treatment fluid into the cylinder of a syringe with the plunger of the syringe extending outwardly from the cylinder and with the cylinder having a front hub portion remote from a notched end plate at the outer end of the plunger, attaching a rubberband to the hub and to the end plate to create a resilient force when the plunger is fully extended from the cylinder to urge the plunger into the cylinder, resisting the inward movement of the plunger by the user applying resistance to the syringe to resist the resilient force of the rubberband, the user inserting the blunt end of the applicating tip of the syringe into a gum pocket of the user, releasing the resistance to permit movement of the plunger into the cylinder and force the treatment fluid out of the applicating tip and into the gum pocket, and flushing the gum pocket with the treatment fluid.

* * * * *